(12) United States Patent
Estevez Company et al.

(10) Patent No.: US 9,157,039 B1
(45) Date of Patent: Oct. 13, 2015

(54) PROCESS FOR MANUFACTURING BIOFUELS

(71) Applicant: INSTITUT UNIV. DE CIENCIA I TECNOLOGIA, S. A., Mollet Del Valles (ES)

(72) Inventors: Carles Estevez Company, Sitges (ES); Natividad Bayarri Ferrer, Badalona (ES); Josep Castells Boliart, Montmelo (ES)

(73) Assignee: INSTITUT UNIV. DE CIÈNCIA I TECNOLOGIA, S.A., Mollet Del Valles (ES)

( * ) Notice: Subject to any disclaimer, the term of this patent is extended or adjusted under 35 U.S.C. 154(b) by 0 days.

(21) Appl. No.: 14/441,686

(22) PCT Filed: Nov. 8, 2013

(86) PCT No.: PCT/EP2013/073345
§ 371 (c)(1),
(2) Date: May 8, 2015

(87) PCT Pub. No.: WO2014/072453
PCT Pub. Date: May 15, 2014

(30) Foreign Application Priority Data

Nov. 9, 2012 (EP) .................................. 12382441
Aug. 20, 2013 (AR) ............................. 20130102941

(51) Int. Cl.
*C11C 3/00* (2006.01)
*C10L 1/02* (2006.01)

(52) U.S. Cl.
CPC ......... *C10L 1/026* (2013.01); *C10L 2200/0476* (2013.01); *C10L 2270/026* (2013.01)

(58) Field of Classification Search
CPC ............ C11C 3/06; C11C 3/04; C11C 3/003; C11C 3/10; C07C 67/03; C07C 67/08554; Y02E 50/13; C10L 1/026
USPC .................................................. 554/168, 169
See application file for complete search history.

(56) References Cited

U.S. PATENT DOCUMENTS

2003/0163949 A1 9/2003 Delfort et al.
2003/0167681 A1 9/2003 Delgado Puche

FOREIGN PATENT DOCUMENTS

WO    WO 2006/048048    5/2006
WO    WO 2008/006860    1/2008
WO    WO 2008006860 A2 * 1/2008

OTHER PUBLICATIONS

PCT Search Report/Written Opinion for PCT/EP2013/073345 prepared Jan. 7, 2014.

* cited by examiner

*Primary Examiner* — Deborah D Carr
(74) *Attorney, Agent, or Firm* — Barnes & Thornburg LLP

(57) ABSTRACT

The present invention relates to a process for obtaining simultaneously several compositions comprising fatty acid alkyl esters (biodiesel), glycerol formal and fatty acid glycerol formal esters.

10 Claims, 3 Drawing Sheets

Composition I: Mixture of fatty acid alkyl esters and fatty acid glycerol formal esters
Composition II: Glycerol formal
Composition III: Fatty acid alkyl esters
Composition IV: Fatty acid glycerol formal esters

PROCESS FOR MANUFACTURING BIOFUELS

CROSS-REFERENCE TO RELATED APPLICATIONS

This application is a national stage entry under 35 USC §371(b) of PCT International Application No. PCT/EP2013/073345, filed Nov. 8, 2013, and claims the benefit of European Patent Application No. 12382441.9, filed on Nov. 9, 2012 and Argentine Patent Application No. 20130102941, filed Aug. 20, 2013, all of which are expressly incorporated by reference herein.

FIELD OF THE INVENTION

The present invention relates to a process for obtaining simultaneously several different compositions useful as bio fuels where the synthetic procedure is characterized by a 100% atom economy.

BACKGROUND OF THE INVENTION

The world has recognized the critical need to decouple economic growth from resource impact. In particular, Europe is aimed at increasing industrial competitiveness whilst drastically reducing resource and energy inefficiencies. The underlying principle is to develop enabling technologies and solutions along the value chain to "do more with less".

The following objectives have been proposed:
1. A reduction in fossil-fuel energy intensity of up to 30% from current levels by 2030 through a combination of, for example cogeneration-heat-power, process intensification, introduction of novel energy-saving processes, and progressive introduction of renewable energy sources within the process cycle.
2. By 2030, up to 20% reduction in non-renewable, primary raw material intensity versus current levels, by increasing chemical and physical transformation yields and/or using secondary and renewable raw materials with proven sustainability advantages.

The traditional manufacture of biodiesel is an area where these principles are most relevant since biodiesel, along with bioethanol, is currently the major biofuel in the market and, in addition, its manufacture is resource inefficient because not all the oil feedstock is converted into biofuel.

The industrial method for biodiesel production currently involves the transesterification of triglycerides with excess methanol in the presence of a catalyst to yield fatty acid methyl esters (the desired fuel product) and glycerol (a byproduct without fuel properties).

The resource inefficiency in a synthesis process is quantified by the atom economy, a well known factor that measures the percentage of atomic mass of starting materials that is incorporated into the desired final product of a chemical reaction, fatty acid methyl esters in this case. The atom economy of biodiesel production is 90% which is an unacceptable value for a large-volume commodity.

On the other hand, obtaining glycerol is a problem since there is a huge uncertainty of a secondary market for large volumes of crude glycerol derived from biodiesel manufacture.

The low atom economy combined with the glycerol market uncertainty contribute significantly to decrease the profitability of a biodiesel manufacturing plant.

U.S. Pat. No. 6,890,364 B2 and US 2004/0025417 A1 to Delfort et al. disclose a process for producing glycerol acetals to be used in diesel fuels. The acetal oxygenate additive is claimed to reduce particulate emissions from diesel engines.

U.S. Pat. No. 5,917,059 to Bruchmann as well as U.S. Pat. Nos. 6,713,640 and 6,548,681 to Miller et al. describe a process for preparing acetals.

EP2476740 (A1) relates to a process for the preparation of a mixture comprising fatty acid alkyl esters and acetals with fuel characteristics. The reaction takes place in a closed vessel and comprises reacting a mixture, obtained from the partial transesterification of a triglyceride with a lower alkanol, comprising glycerol, monoglycerides, diglycerides, triglycerides, fatty acid alkyl esters, and excess alkanol with an aldehyde, ketone or diether as a glycerol acetal forming agent in the presence of a solid acid catalyst to form a mixture of the fatty acid alkyl ester and the acetal of the glycerol to provide the composition.

However, none of these documents provides a process for obtaining simultaneously several compositions comprising fatty acid alkyl esters (biodiesel), glycerol formal and the bioester of fatty acid glycerol formal ester, starting from natural oils (triglycerides). The importance for obtaining glycerol formal resides in two facts: the first is that glycerol formal is the lowest possible molecular weight acetal that can be prepared from glycerol; the second is that glycerol formal is the starting material for the preparation of fatty acid glycerol formal esters, a glycerol-containing bioester with fuel characteristics similar to biodiesel. The possibility for obtaining the lowest possible molecular weight glycerol acetal (glycerol formal) is extremely relevant for the fuel properties of the fuel compositions that can be prepared from these components as already disclosed in EP 2049623.

It is therefore an object of the present invention to provide a flexible synthetic process that transforms efficiently triglycerides and glycerol into a variety of fuels whose actual compositions depend on the specific selection of raw materials and reaction conditions.

It is a further object of the present invention to provide a range of compositions useful as bio fuels in both automotive and industrial applications (e.g. in industrial boilers).

DESCRIPTION OF THE INVENTION

Figure 3:
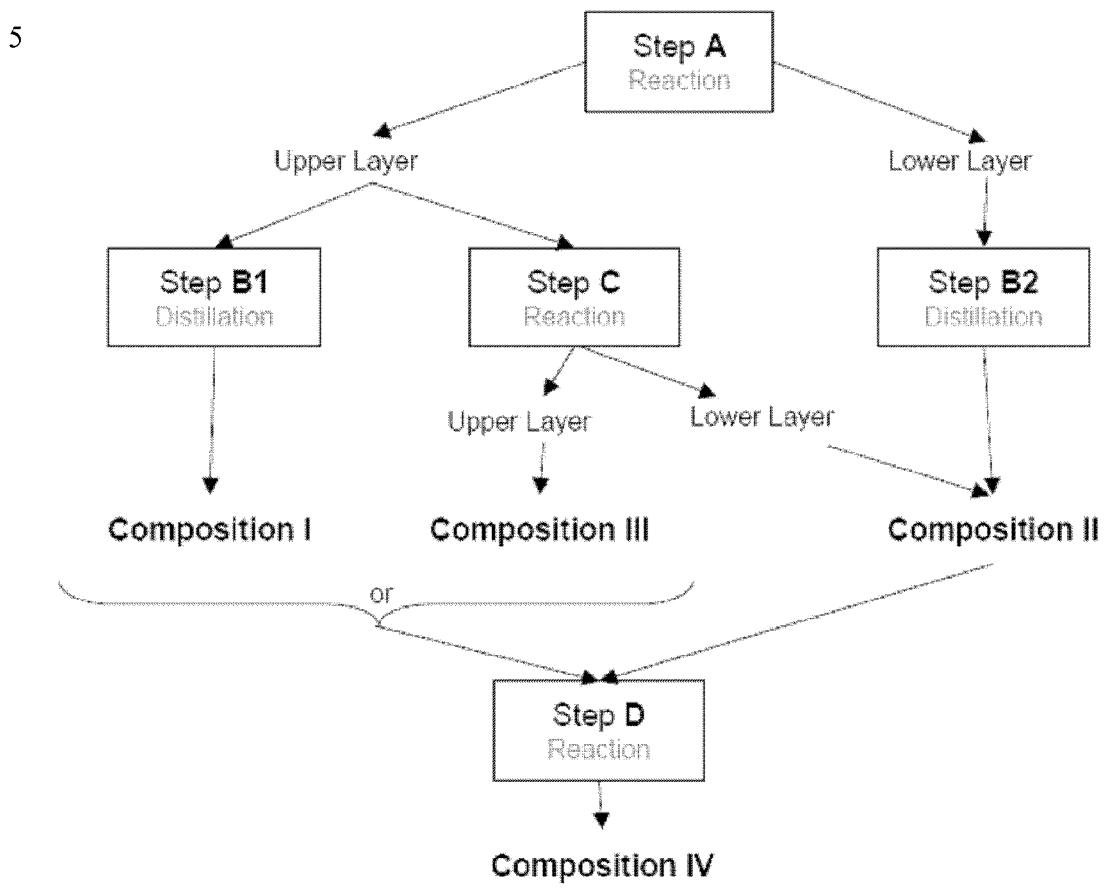
FIG. 3 shows the whole process disclosed herein indicating the different steps and the compositions which are obtained.

The present invention relates to a process for obtaining simultaneously several compositions comprising fatty acid alkyl esters (biodiesel), glycerol formal and the bioester of fatty acid glycerol formal ester. FIG. 3 shows the whole process indicating the different steps and the compositions which are obtained.

Said process comprises the following steps:

(A) Reacting triglyceride, glycerol, preferably glycerol containing water, and dialkoxymethane, preferably dimethoxymethane, in the presence of an acid catalyst, preferably wherein the molar ratio of triglyceride to dialkoxymethane is between 1 to 6 and 1 to 30, wherein the molar ratio of triglyceride to glycerol is between 1 to 3 and 1 to 7 and wherein the dialkoxymethane contains 3 to 9 carbon atoms, thus forming two layers when the reaction is over.

Note that in the context of the present invention when a numeric range is mentioned, for example "1 to 6", both ends, for example "1" and "6" are also included in said range, as well as each of the single possibilities in the range, for example "2", "3", "4," or "5".

Preferably, said catalyst is an homogeneous liquid, more preferably sulphuric acid, or said catalyst is heterogeneous, preferably an acidic ionic exchange resin.

This step (A) is usually carried out at a high temperature, preferably between 55 and 85° C. and more preferably at around 70° C. for the homogeneous catalysis and at 85° C. for the heterogeneous catalysis. The triglyceride to be used in this step has a natural origin (plant or animal) and includes, but without being limited thereto, sunflower oil, soy oil, coconut oil, palm oil, fats from cow, chicken, etc., and even used cooking oil can also be re-used.

The upper layer comprises a mixture of fatty acid alkyl esters (fatty acid methyl ester if dimethoxymethane has been used in step (A)), fatty acid glycerol formal esters and an excess of dialkoxymethane and alkyl alcohol (methanol if dimethoxymethane has been used in step (A)). The lower layer comprises a mixture of glycerol formal, excess glycerol and catalyst if an homogeneous catalyst, in particular polar catalyst, has been used (for example, sulphuric acid).

Accordingly, if the dialkoxymethane is dimethoxymethane in step (A), fatty acid methyl esters and methanol are obtained in the upper layer along with fatty acid glycerol formal esters and an excess of dimethoxymethane.

(B1) Separating usually by distillation the dialkoxymethane and the alkyl alcohol from the upper layer, constituting the remaining components (fatty acid alkyl esters and fatty acid glycerol formal esters) the composition I.

The excess of dialkoxymethane and alkyl alcohol is reused in the process. In particular, if the alkyl alcohol is methanol, this can be used in conventional biodiesel manufacture or recycled into dimethoxymethane through a conventional process in which methanol is oxidized to formaldehyde which, in a subsequent step, undergoes acetalization with methanol itself producing again dimethoxymethane If necessary, any trace of acid present in said composition A can be neutralized.

(B2) Separating usually by distillation the glycerol formal from the mixture of unreacted glycerol and catalyst from the lower layer (catalyst would only be present if homogeneous catalysis has been performed) for obtaining a composition II comprising glycerol formal. The mixture of unreacted glycerol and homogeneous catalyst can be re-used into the process.

This is clearly a fundamental advantage since glycerol formal has much better fuel properties than glycerol and, in addition, can be converted into fatty acid glycerol formal ester (see step (D)).

Figure 1:
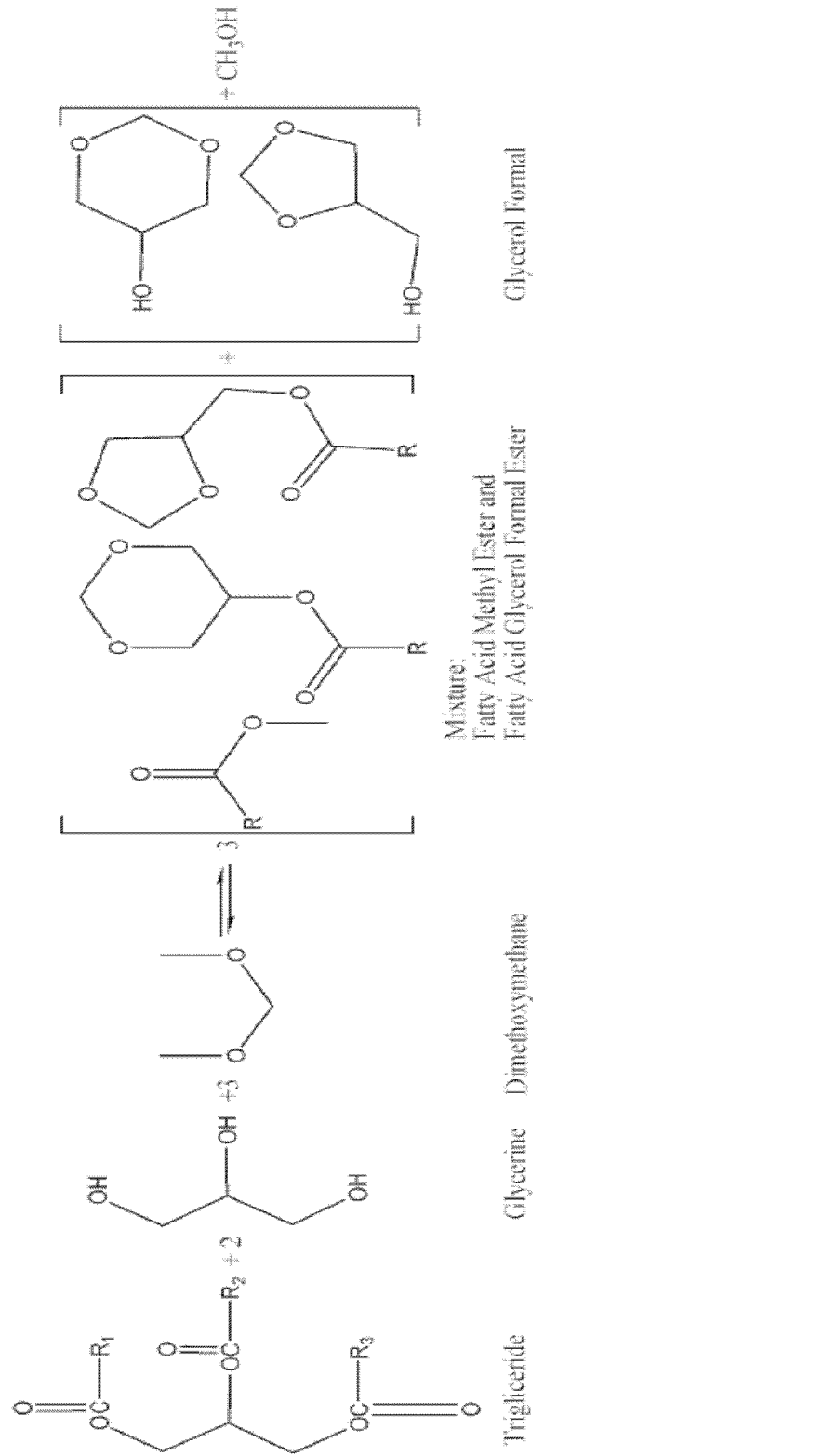
FIG. 1 shows the reactions involved in the process of the invention (steps A-B1/B2-C) for obtaining compositions I, II, and IV.

Steps A-B1/B2 are shown in FIG. 1.

(C) instead of step B1, the compounds in the upper layer (fatty acid alkyl esters, fatty acid glycerol formal esters, dialkoxymethane and alkyl alcohol) can be reacted with a mixture of alkyl alcohol and homogeneous or heterogeneous acid catalyst in order to transform the fatty acid glycerol formal ester into fatty acid alkyl ester. Subsequently, the mixture is neutralized and the excess dialkoxymethane and alkyl alcohol are removed for example by decantation. As a result, two layers are formed. The resulting fatty acid alkyl esters are in the upper layer. Glycerol formal, a by-product of this reaction, remains in the lower layer and is usually isolated by distillation. Accordingly, from this step a composition III comprising fatty acid alkyl esters is obtained along with composition II comprising glycerol formal.

If the dialkoxymethane is dimethoxymethane in step (C) and alkyl alcohol is methanol, the upper layer will comprise fatty acid methyl ester (FAME) which is the fundamental constituent of commercial biodiesel.

Preferably, said homogeneous acid catalyst is sulphuric acid and said heterogeneous acid catalyst is an acidic ionic exchange resin.

(D) Carrying out a transesterification reaction between Composition I comprising fatty acid alkyl esters and fatty acid glycerol formal esters or Composition III comprising fatty acid alkyl esters and Composition II comprising glycerol formal, in the presence of a transesterification catalyst to forma composition comprising fatty acid glycerol formal esters (composition IV), preferably wherein the mole ratio between fatty acid alkyl esters and glycerol formal is between 1 to 1 and 1 to 5.

Preferably, the transesterification catalyst is a titanium alkoxide wherein the alkoxide group contains 1 to 6 carbon atoms.

Figure 2:
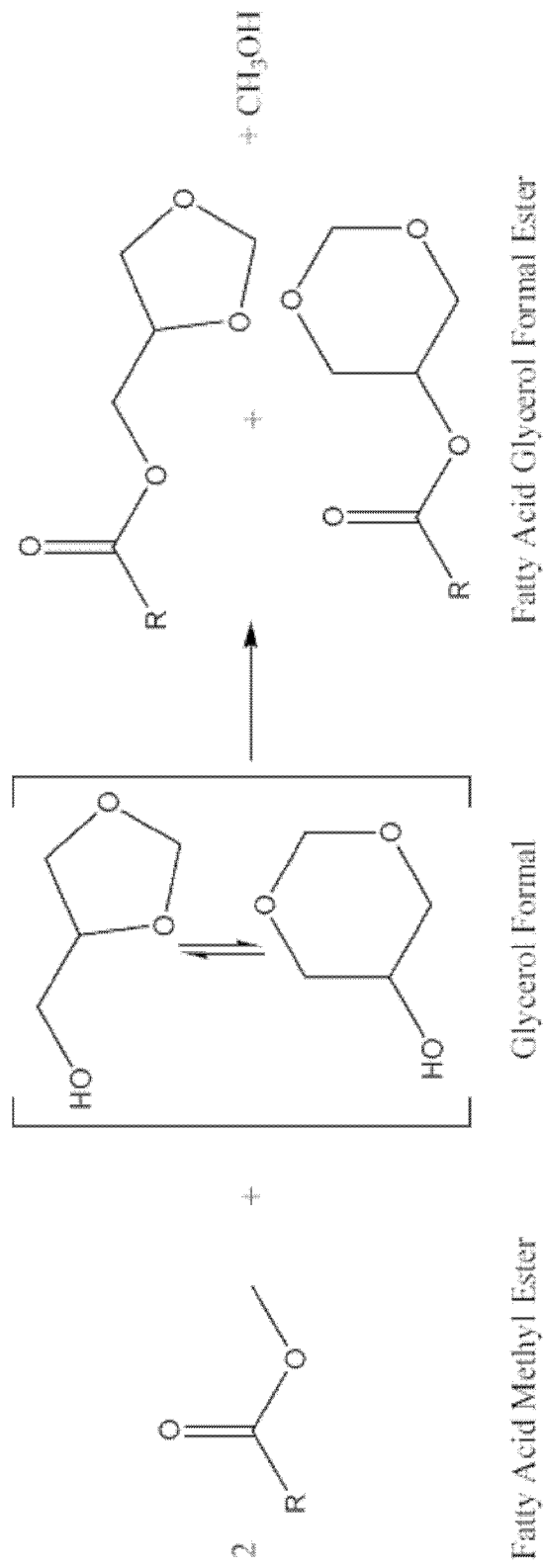
FIG. 2 shows the additional reaction (step D) for obtaining compositions II and III.

FIG. 2 depicts the chemical synthesis of step (D).

If necessary, additional non-reactive compounds (additives) may be added to the reaction vessels so that the final compositions (I, II, III or IV) may also include such additives or may be added once the final compositions are obtained. Examples of additives include, but not limited thereto, one or more additional components selected from the group consisting of: antioxidants, agents for increasing the octane number, biocides, chelating agents, detergents, dispersants, solvents, corrosion inhibitors, oxide inhibitors, and cetane improvers.

The main advantages of the overall process are: 1) the process does not generate any by-product, 2) the process does not generate water, 3) the process can be integrated fairly easily to current biodiesel production systems and 4) similarly to biodiesel, the process uses any suitable source of triglycerides, in particular classical oil seeds but also non-food plant crops such as Jatropha Curcas or non-edible animal fats, 5) allows the conversion of a conventional biodiesel manufacturing plant in order to obtain FAME and glycerol formal instead of FAME and glycerol.

The process disclosed herein, including all the possible embodiments, can be carried out as a continuous process or as a batch or discontinuous process.

The present invention also relates to the products directly obtained by the process as disclosed in the present invention, i.e. composition I (fatty acid alkyl esters and fatty acid glycerol formal esters), composition II (glycerol formal), composition III (fatty acid alkyl esters) and composition IV (fatty acid glycerol formal esters). Preferably the fatty acid alkyl esters are fatty acid methyl esters.

The present invention also relates to the use of the composition I as biofuel, for example as automotive fuel or heating oil.

The present invention further relates to the use of the composition II as bio fuel in industrial applications, for example as heating oil.

The present invention further relates to the use of the compositions III or IV as biofuel, for example as automotive fuel or heating oil.

The following Examples are offered for illustrative purposes only and are not intended to limit the scope of the present invention in any way.

EXAMPLES

Process for Obtaining Compositions I and II

As indicated in the description above, any of the following processes may contain further additives as those disclosed above.

Example 1

Homogeneous Catalysis 79.0 g of soy oil (0.093 mol, 1.000 eq), 28.12 g of glycerol (99% glycerol w/w) (0.306 mol, 3.305 eq), 105.78 g of dimethoxymethane (1.390 mol, 15.03 eq), and 6.32 g of sulfuric acid (0.064 mol, 0.697 eq.) were added to a closed vessel. The mixture was stirred at 290 rpm and heated at 70° C. The reaction mixture was maintained at 70° C. and 1.5 bar for 10 hours. Two layers were separated by decantation. The upper layer containing excess of dimethoxymethane, methanol and a mixture of fatty acid methyl esters and fatty acid glycerol formal esters was subjected to distillation at atmospheric pressure. The fraction distilled at 42° C. corresponds to pure dimethoxymethane (82.40 g, 1.083 mol, 11.71 eq) which is recycled in the process without further treatment. Subsequently, a fraction distilling at 65° C. corresponding to pure methanol (9.32 g, 0.291 mol, 3.145 eq.) was obtained. The resulting mixture after distillation of volatile compounds was neutralised with an aqueous solution of potassium hydroxide (10% w/w) to remove traces of sulfuric acid and then water was added. The mixture was dried yielding 90.69 g of a product containing fatty acid methyl esters and fatty acid glycerol formal esters (87:13 w/w) (Composition I). The glycerol formal in the lower layer is distilled off at reduced pressure to obtain 25.75 g of a fraction distilling at 90° C. corresponding to glycerol formal (0.248 mol, 2.677 eq.) (Composition II). The residue of distillation which comprises unreacted glycerol (4.58 g, 0.050 mol, 0.538 eq.) and sulfuric acid are re-used in subsequent batches.

Example 2

Homogeneous Catalysis 70.90 g of soy oil (0.083 mol, 1.000 eq), 31.91 g of glycerol (99% glycerol w/w) (0.347 mol, 4.177 eq), 165.84 g of dimethoxymethane (2.179 mol, 26.24 eq), and 7.44 g of sulfuric acid (0.076 mol, 0.914 eq.) were added to a closed vessel. The mixture was stirred at 290 rpm and heated at 70° C. The reaction mixture was maintained at 70° C. and 1.5 bar for 2 hours. Two layers were separated by decantation. The upper layer containing excess of dimethoxymethane, methanol and a mixture of fatty acid methyl esters and fatty acid glycerol formal esters was neutralised with a basic ion exchange resin and then subjected to distillation at atmospheric pressure. The fraction distilled at 42° C. corresponds to pure dimethoxymethane (122.37 g, 1.608 mol, 19.369 eq) which is recycled in the process without further treatment. Subsequently, a fraction distilling at 65° C. corresponding to pure methanol (14.82 g, 0.462 mol, 5.571 eq.) was obtained. The resulting mixture was dried yielding 90.25 g of a product containing fatty acid methyl esters and fatty acid glycerol formal esters (95:5 w/w) (Composition I). The lower layer was then distilled at reduced pressure to obtain 33.71 g of a fraction distilling at 90° C. corresponding to glycerol formal (0.323 mol, 3.892 eq.) (Composition II). The residue of distillation which comprises unreacted glycerol (7.80 g, 0.085 mol, 1.021 eq.) and sulfuric acid are re-used in subsequent batches.

Example 3

Heterogeneous Catalysis 143.60 g of soy oil (0.168 mol, 1.000 eq), 46.24 g of glycerol (99% glycerol w/w) (0.503 mol, 2.989 eq), 210.09 g of dimethoxymethane (2.761 mol, 16.418 eq), and 17.66 g of an acidic ionic exchange resin were added to a closed vessel. The mixture was stirred at 290 rpm and heated at 85° C. The reaction mixture was maintained at 85° C. and 1.5 bar for 6 hours. The catalyst was then filtered and the resulting mixture was distilled at atmospheric pressure. The fraction distilled at 42° C. corresponds to pure dimethoxymethane (168.16 g, 2.210 mol, 13.141 eq) which is recycled in the process without further treatment. Subsequently, a fraction distilling at 65° C. corresponding to pure methanol (14.36 g, 0.448 mol, 2.665 eq.) was obtained. The resulting mixture after evaporation of volatile compounds was decanted forming two layers. The upper layer containing the mixture of fatty acid methyl esters and fatty acid glycerol formal esters was subjected to a first wash with an aqueous solution of potassium hydroxide (10% w/w) and a second wash with water. The mixture was dried yielding 155.81 g of a product containing fatty acid methyl esters and fatty acid glycerol formal esters (94:6 w/w) (Composition I). The lower layer was then distilled at reduced pressure to obtain 54.28 g of a fraction distilling at 90° C. corresponding to glycerol formal (0.522 mol, 3.104 eq.) (Composition II). The residue of distillation which contains unreacted glycerol (1.44 g, 0.016 mol, 0.093 eq.) is re-used in subsequent batches.

Example 4

Heterogeneous Catalysis 141.80 g of soy oil (0.166 mol, 1.000 eq), 44.95 g of glycerol (99% glycerol w/w) (0.489 mol, 2.943 eq), 207.74 g of dimethoxymethane (2.730 mol, 16.440 eq), and 14.61 g of an acidic ionic exchange resin were added to a closed vessel. The mixture was stirred at 290 rpm and heated at 85° C. The reaction mixture was maintained at 85° C. and 1.5 bar for 5 hours. The catalyst was then filtered and the resulting mixture was distilled at atmospheric pressure. The fraction distilled at 42° C. corresponds to pure dimethoxymethane (172.71 g, 2.270 mol, 13.668 eq) which is recycled in the process without further treatment. Subsequently, a fraction distilling at 65° C. corresponding to pure methanol (14.61 g, 0.456 mol, 2.745 eq.) was obtained. The resulting mixture after evaporation of volatile compounds was decanted forming two layers. The upper layer containing the mixture of fatty acid methyl esters and fatty acid glycerol formal esters was subjected to a first wash with an aqueous solution of potassium hydroxide (10% w/w) and a second wash with water. The mixture was dried yielding 145.91 g of a product containing fatty acid methyl esters and fatty acid glycerol formal esters (95:5 w/w) (Composition I). The lower layer was then distilled at reduced pressure to obtain 51.05 g of a fraction distilling at 90° C. corresponding to glycerol formal (0.491 mol, 2.956 eq.) (Composition II). The residue of distillation which contains unreacted glycerol (5.10 g, 0.055 mol, 0.334 eq.) is re-used in subsequent batches.

Process for Obtaining Compositions II and III

Example 5

80.5 g of soy oil (0.09 mol, 1.0 eq), 25.9 g of glycerol (99% glycerol w/w) (0.28 mol, 3 eq), 215.3 g of dimethoxymethane (2.82 mol, 30 eq), and 6.4 g of sulfuric acid were added to a closed vessel. The mixture was stirred at 270 rpm and heated at 70° C. The reaction mixture was maintained at 70° C. and 1.5 bar for 4 hours. the two obtained layers were separated. The upper layer containing excess of dimethoxymethane and methanol along with a mixture of fatty acid methyl esters and fatty acid glycerol formal esters was refluxed with 30 g of a methanolic solution of sulfuric acid (5% w/w). Two layers were separated. The upper layer was neutralized using an ion-exchange resin (basic form). After filtration, excess of dimethoxymethane and methanol were distilled-off yielding 78.1 g of a product containing fatty acid methyl esters (Composition III). The glycerol formal in the lower layer was distilled off to obtain 26 g of a pure product (Composition II). The residue of distillation which comprises unreacted glycerol and sulfuric acid was re-used in subsequent batches.

Process for Obtaining Composition IV

Example 6

Glycerol formal (1354 g, 13.0 mol, 2 eq), and fatty acid methyl esters (1900 g, 6.5 mol, 1 eq) were added to a reactor equipped with a vacuum distillation system. The mixture was heated at 100° C. and titanium isopropoxide was added. The reaction mixture was kept at 100° C. and 10 mbar pressure for 12 hours. The distilled-off methanol (190 g, 5.93 mol, 0.91 eq) was collected in a distillation collector. Once the reaction is over, the excess of glycerol formal was distilled off at 20 min Hg reduced pressure. The fraction distilling at 90° C. corresponds to pure glycerol formal. Subsequently, the reaction mixture was cooled to room temperature. Water (190 g) was added and the reaction mixture was stirred for 30 minutes in order to hydrolyze the catalyst. The hydrolyzed catalyst was removed by centrifugation and washed with hexane and subsequently evaporated to dryness. The resulting orange oil was filtered through a 0.45 micrometer filter to yield 1735 g of fatty acid glycerol formal esters.

What is claimed is:

1. Process for obtaining simultaneously several compositions comprising fatty acid alkyl esters, glycerol formal and the bioester fatty acid glycerol formal ester, comprising the steps of:
   (A) reacting triglyceride, glycerol and dialkoxymethane in the presence of an acid homogeneous or heterogeneous catalyst, thus forming two layers, wherein the upper layer comprises a mixture of fatty acid alkyl esters, fatty acid glycerol formal esters and an excess of dialkoxymethane and alkyl alcohol and the lower layer comprises a mixture of glycerol formal, excess glycerol, and homogeneous catalyst if an homogeneous catalyst has been used in the reaction;
   (B1) separating the dialkoxymethane and the alkyl alcohol from the upper layer for obtaining a composition comprising fatty acid alkyl esters and fatty acid glycerol formal esters;
   or instead of step (B1), (C) reacting the compounds from the upper layer obtained according to step (A) with a mixture of alkyl alcohol and acid catalyst for obtaining a composition comprising fatty acid alkyl esters and a composition comprising glycerol formal;
   (B2) separating the glycerol formal from unreacted glycerol and the homogeneous catalyst if an homogeneous catalyst has been used in step (A) from the lower layer for obtaining a composition comprising glycerol formal;
   (D) carrying out a transesterification reaction between the composition obtained in step (B1) or the composition comprising fatty acid alkyl esters obtained in step (C) and the composition comprising glycerol formal obtained in step (C) in the presence of a transesterification homogeneous or heterogeneous catalyst to form a composition comprising fatty acid glycerol formal ester.

2. Process according to claim 1, wherein the glycerol used in step (A) further contains water.

3. Process according to claim 1, wherein in the step (A) the molar ratio of triglyceride to dialkoxymethane is between 1 to 6 and 1 to 30, the molar ratio of triglyceride to glycerol is between 1 to 3 and 1 to 7 and wherein the dialkoxymethane contains 3 to 9 carbon atoms.

4. Process according to claim 1, wherein in the step (A) if the dialkoxymethane is dimethoxymethane, fatty acid methyl ester and methanol are obtained in the upper layer along with fatty acid glycerol formal esters and an excess of dimethoxymethane.

5. Process according to claim 1, wherein the acid catalyst used in step (A) is an homogeneous catalyst which is sulphuric acid or an heterogeneous catalyst which is an acidic ionic exchange resin.

6. Process according to claim 1, wherein the temperature of reaction of step (A) is between 55° C. and 85° C.

7. Process according to claim 1, wherein the transesterification catalyst used in step (D) is a titanium alkoxide, wherein the alkoxide group contains 1 to 6 carbon atoms.

8. Process according to claim 1, wherein the excess of dialkoxymethane and the alkyl alcohol from step (B1) and the unreacted glycerol and homogeneous catalyst if an homogeneous catalyst has been used in step (A) from step (B2) can be reused or recycled into the process.

9. Process according to claim 1, wherein in the step (C) the alkyl alcohol is methanol and the fatty acid alkyl ester is fatty acid methyl ester if dimethoxymethane has been used in said step (C) as a reagent.

10. Process according to claim 1, wherein the acid catalyst used in step (C) is an homogeneous catalyst which is sulphuric acid or an heterogeneous catalyst which is an acidic ionic exchange resin.

* * * * *